(12) United States Patent
Kong et al.

(10) Patent No.: US 11,860,113 B2
(45) Date of Patent: Jan. 2, 2024

(54) TUBE WELD X-RAY INSPECTION DEVICE COMPRISING AN X-RAY SOURCE, AN X-RAY SOURCE SUPPORT, AND AN IMAGE PLATE FIXING PART FOR FIXING AN IMAGE PLATE

(71) Applicant: DIGIRAY CORP., Goyang-si (KR)

(72) Inventors: Sang Sub Kong, Goyang-si (KR); Young Ho Kang, Goyang-si (KR); Nam Woo Kim, Sejong-si (KR)

(73) Assignee: DIGIRAY CORP., Goyang-si (KR)

( * ) Notice: Subject to any disclaimer, the term of this patent is extended or adjusted under 35 U.S.C. 154(b) by 75 days.

(21) Appl. No.: 17/525,343

(22) Filed: Nov. 12, 2021

(65) Prior Publication Data
US 2022/0317064 A1    Oct. 6, 2022

(30) Foreign Application Priority Data

Mar. 30, 2021 (KR) .......... 10-2021-0041440
Mar. 30, 2021 (KR) .......... 10-2021-0041442

(51) Int. Cl.
*G01N 23/04* (2018.01)
*G01N 23/087* (2018.01)
*G01N 23/18* (2018.01)
*G01N 23/083* (2018.01)
*G01T 1/20* (2006.01)

(52) U.S. Cl.
CPC .............. *G01N 23/18* (2013.01); *G01N 23/04* (2013.01); *G01N 23/043* (2013.01); *G01N 23/083* (2013.01); *G01N 23/087* (2013.01); *G01T 1/2012* (2013.01); *G01T 1/2014* (2013.01); *G01N 2223/04* (2013.01); *G01N 2223/3303* (2013.01); *G01N 2223/40* (2013.01); *G01N 2223/407* (2013.01); *G01N 2223/507* (2013.01); *G01N 2223/629* (2013.01); *G01N 2223/646* (2013.01)

(58) Field of Classification Search
CPC .... G01N 23/04; G01N 23/043; G01N 23/044; G01N 23/046; G01N 23/083; G01N 23/087; G01N 23/16; G01N 23/18; G01N 2223/03; G01N 2223/04; G01N 2223/1016; G01N 2223/3303; G01N 2223/407; G01N 2223/629; G01N 2223/646; G01T 1/2012; G01T 1/2014
USPC .................. 378/51, 53–55, 57–60, 121, 122; 250/580–591
See application file for complete search history.

(56) References Cited

U.S. PATENT DOCUMENTS 3,752,990 A * 8/1973 Fischer ................... H05G 1/04
378/38
3,873,837 A * 3/1975 Palermo, Jr. ......... G01N 23/083
378/61
(Continued)

FOREIGN PATENT DOCUMENTS

CN    209589884 U    11/2019
CN    110987983 A     4/2020
(Continued)

*Primary Examiner* — Allen C. Ho
(74) *Attorney, Agent, or Firm* — Birch, Stewart, Kolasch & Birch, LLP

(57) ABSTRACT

Provided is a tube weld X-ray inspection device for inspecting an abnormality, such as a tube welding part crack, of a heat exchanger by using X-rays.

20 Claims, 4 Drawing Sheets

(56) References Cited

U.S. PATENT DOCUMENTS

| | | | | |
|---|---|---|---|---|
| 3,906,358 | A | * | 9/1975 | Stone .................... G01N 27/902 378/59 |
| 3,958,120 | A | * | 5/1976 | Ward .................... G03B 42/028 378/197 |
| 3,994,173 | A | * | 11/1976 | Ward .................... G01N 27/9093 73/866.5 |
| 4,078,180 | A | * | 3/1978 | Green .................... G01N 23/043 378/162 |
| 4,567,012 | A | * | 1/1986 | Radcliff .................... G01N 23/04 378/54 |
| 5,177,779 | A | * | 1/1993 | Cornu .................... G01N 23/04 378/205 |
| 6,137,860 | A | * | 10/2000 | Ellegood .................... G01N 23/046 228/104 |
| 7,008,559 | B2 | * | 3/2006 | Chen .................... C09K 11/574 252/301.4 R |
| 7,067,072 | B2 | * | 6/2006 | Chen .................... C09K 11/574 252/301.36 |
| 9,524,546 | B2 | * | 12/2016 | Nagashima .................... G06T 7/001 |
| 10,168,288 | B2 | * | 1/2019 | Bueno .................... G01N 23/083 |
| 10,732,131 | B2 | * | 8/2020 | Schmitz .................... G01N 23/04 |
| 2003/0064532 | A1 | | 4/2003 | Chen |
| 2016/0370303 | A1 | | 12/2016 | Schmitz et al. |

FOREIGN PATENT DOCUMENTS

| | | |
|---|---|---|
| JP | 58-86444 A | 5/1983 |
| JP | 7-214370 A | 8/1995 |
| JP | 2001-83277 A | 3/2001 |
| JP | 2012-77778 A | 4/2012 |
| KR | 10-1984-0002103 A | 6/1984 |
| KR | 20-0333602 Y1 | 11/2003 |
| KR | 20-0377998 Y1 | 3/2005 |
| KR | 10-2006-0030452 A | 4/2006 |
| KR | 20-2010-0012460 U | 12/2010 |
| KR | 10-1252796 B1 | 4/2013 |
| KR | 10-1263750 B1 | 5/2013 |
| KR | 10-1298703 B1 | 8/2013 |
| KR | 10-1477636 B1 | 12/2014 |
| KR | 10-1516150 B1 | 5/2015 |
| KR | 10-1855599 B1 | 6/2018 |
| KR | 10-2020-0130961 A | 11/2020 |
| KR | 10-2303823 B1 | 9/2021 |
| KR | 10-2303826 B1 | 9/2021 |
| KR | 10-2303838 B1 | 9/2021 |
| WO | WO2010/151171 A | 12/2010 |

* cited by examiner

TUBE WELD X-RAY INSPECTION DEVICE COMPRISING AN X-RAY SOURCE, AN X-RAY SOURCE SUPPORT, AND AN IMAGE PLATE FIXING PART FOR FIXING AN IMAGE PLATE

CROSS REFERENCE TO RELATED APPLICATION

The present application claims priorities to Korean Patent Application Nos. 10-2021-0041440 and 10-2021-0041442, filed Mar. 30, 2021, the entire contents of which are incorporated herein for all purposes by this reference.

BACKGROUND OF THE INVENTION

Field of the Invention

The present disclosure relates to a tube weld X-ray inspection device. More particularly, the present disclosure relates to a tube weld X-ray inspection device for inspecting an abnormality, such as a tube welding part crack, of a heat exchanger by using X-rays.

Description of the Related Art

A shell and tube heat exchanger is a typical heat exchanger, and is composed of two tube sheets and multiple tubes connecting the two tube sheets, and the outside thereof is a cylindrical shell having a airtight structure. The shell and tube heat exchanger is used for various types of heat exchange, such as heating, cooling, condensation, vaporization, etc.

As a fluid flows into and out of the tubes and a different fluid flows into and out of the space outside the tubes, heat exchange is made between the fluids. In general, as the fluid flowing into the space outside the tubes, a fluid, for example, water, or seawater, at room temperature is used.

As the fluid flowing into the tubes, gas is used. However, no limitation thereto is imposed.

Outside the tubes, multiple baffle plates may be formed to form a zigzag flow path of the fluid.

The tube sheets have multiple insertion holes formed therein. With the tubes inserted in the respective insertion holes of the tube sheets, the connection parts of the tubes and the tube sheets are jointed by welding, so that the fluid inside the tubes and the fluid outside the tubes are prevented from mixing. That is, the fluids are prevented from permeating (leaking) between the tubes and the tube sheets.

For devices, for example, a shell and tube heat exchanger, in which multiple tubes are joined by welding, it is necessary to inspect seam portions.

In pipes connected by welding, welds are formed. When connection parts of the pipes are melted and welded, such welds are melted and cooled and thus the structures are recrystallized. Therefore, the welds are weaker in strength than other parts of the pipes.

In addition, welds vary in welding state according to a worker's skill. For example, if the welding time is too long or short, the weld is not strong. Alternatively, if there are many pores or impurities in the weld, the strength is significantly weak.

If the weld, which itself is weaker in strength than other parts, is made to be weaker by the work of an unskilled person or external influences, such as existence of pores or impurities, a crack may appear in a short time in use and the fluid may leak through the weld. If such crack proceeds for a long time, the weld is finally damaged and the pipe in use loses its function.

Therefore, before being buried and used, the welded pipes are inspected for various safety levels including strength, by using an inspection device.

Korean Patent Application Publication No. 10-1984-0002103 discloses "FLUOROSCOPIC EXAMINATION OF PIPE GIRTH WELDS".

The foregoing is intended merely to aid in the understanding of the background of the present disclosure, and is not intended to mean that the present disclosure falls within the purview of the related art that is already known to those skilled in the art.

DOCUMENT OF RELATED ART (Patent Document 1) Korean Patent Application Publication No. 10-1984-0002103 (Publication date: 11 Jun. 1984).

SUMMARY OF THE INVENTION

Accordingly, the present disclosure has been made keeping in mind the above problems occurring in the related art, and the present disclosure is directed to providing a tube weld X-ray inspection device for inspecting an abnormality, such as a tube welding part crack, of a heat exchanger by using X-rays.

The objective of the embodiments of the present disclosure is not limited to the above-described objective, and other objectives which are not described herein will be come apparent to those skilled in the art from the following description.

According to an embodiment of the present disclosure, there is provided a tube weld X-ray inspection device including: an X-ray support provided in a length direction so that the X-ray support is inserted into a tube; an X-ray source provided at a side of the X-ray support in the length direction thereof, and emitting X-rays; and an IP (Image Plate) fixing part for fixing an image plate in a direction perpendicular to an axis of the length direction of the X-ray support while being spaced a predetermined distance from the X-ray source, the image plate absorbing the X-rays and storing the X-rays in a form of energy.

According to the embodiment of the present disclosure, the tube weld X-ray inspection device can easily inspect abnormality of a welding part, such as a tube welding part crack, of a heat exchanger by using X-rays.

In addition, a three-dimensional image highlighting a problem portion can be obtained.

In addition, as the IP fixing part is movable along the X-ray support, it is easy to adjust the depth at which the X-ray source is inserted into the tube.

In addition, because the image plate is attachable and detachable, the image plate can be applied variably depending on a measurement target, so that tube welding parts in various sizes can be inspected.

In addition, the image plate is provided in a shape of a plate with a hollow center, so that it is easy to replace the image plate and move the image plate along the X-ray support.

In addition, by using the image plate in a single integrated piece, image loss or image distortion can be prevented from occurring at the seam portion.

In addition, by providing a reader, there is no need to take the image plate apart to obtain an image, thus reducing a re-photographing time.

In addition, while either the image plate or the reader is rotated and the other is fixed, the reader obtains information of the image plate, so that there is no need to take apart and insert the image plate, thus reducing an image acquisition time.

In addition, the reader is moved to appropriate positions before and after X-ray photograph, so that a re-photographing time can be reduced.

In addition, by providing an initialization module, there is no need to take the image plate apart to initialize the image plate, thus reducing a re-photographing time.

In addition, while either the image plate or the initialization module is rotated and the other is fixed, the initialization module initializes the image plate, so that there is no need to take apart and insert the image plate, thus reducing a re-photographing time.

In addition, the initialization module is moved to appropriate positions before and after X-ray photography, so that a re-photographing time can be reduced.

BRIEF DESCRIPTION OF THE DRAWINGS

The above and other objectives, features, and other advantages of the present disclosure will be more clearly understood from the following detailed description when taken in conjunction with the accompanying drawings, in which.

DETAILED DESCRIPTION OF THE INVENTION

Figure 1:
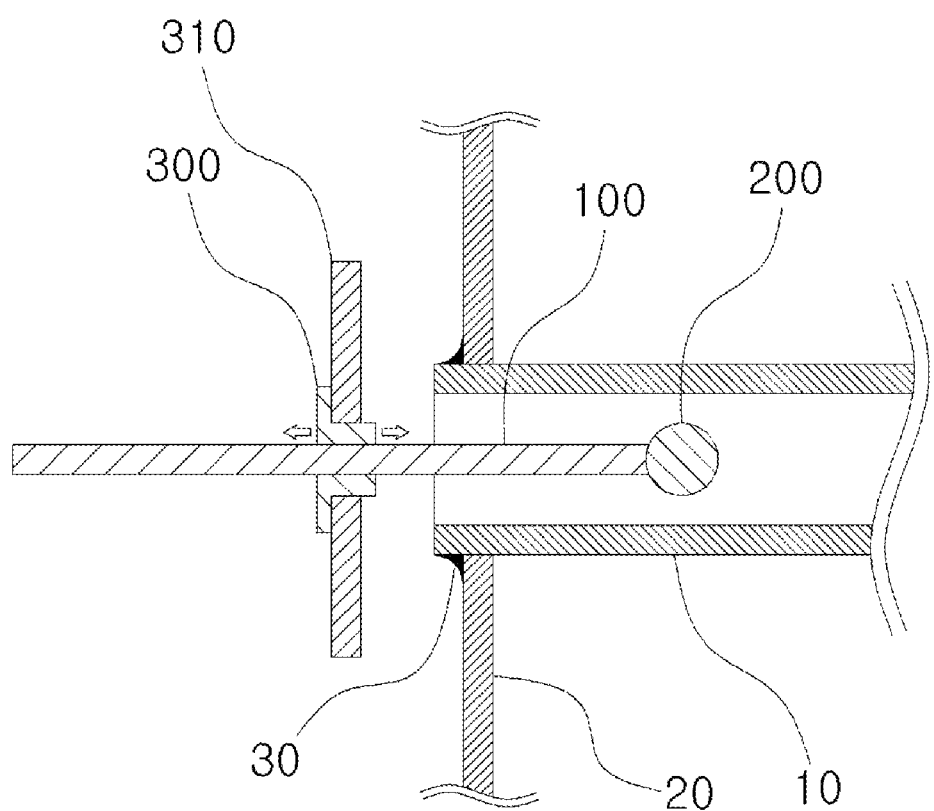
FIG. 1 is a conceptual diagram illustrating a tube weld X-ray inspection device according to an embodiment of the present disclosure.

The present disclosure may be modified in various ways and implemented by various embodiments, so that specific embodiments are shown in the drawings and will be described in detail. However, the present disclosure is not limited thereto, and the exemplary embodiments can be construed as including all modifications, equivalents, or substitutes in a technical concept and a technical scope of the present disclosure.

It will be understood that when an element is referred to as being coupled or connected to another element, it can be directly coupled or connected to the other element or intervening elements may be present therebetween.

In contrast, it will be understood that when an element is referred to as being "directly coupled" or "directly connected" to another element, there are no intervening elements present.

The terms used in the present specification are merely used to describe particular embodiments, and are not intended to limit the present disclosure. As used herein, the singular forms "a", "an", and "the" are intended to include the plural forms as well, unless the context clearly indicates otherwise. In the present specification, it is to be understood that terms such as "including", "having", etc. are intended to indicate the existence of the features, numbers, processes, actions, elements, parts, or combinations thereof disclosed in the specification, and are not intended to preclude the possibility that one or more other features, numbers, processes, actions, elements, parts, or combinations thereof may exist or may be added.

Unless otherwise defined, all terms including technical and scientific terms used herein have the same meaning as commonly understood by those skilled in the art to which the present disclosure pertains. It will be further understood that terms used herein should be interpreted as having a meaning that is consistent with their meaning in the context of this specification and the relevant art and will not be interpreted in an idealized or overly formal sense unless expressly so defined herein.

Hereinafter, the present disclosure will be described in more detail with reference to the accompanying drawings. Prior to offering the description, the terms or words used in the present specification and claims should not be interpreted as being limited to typical meanings or dictionary definitions, but should be interpreted as having meanings and concepts relevant to the technical scope of the present disclosure based on the rule according to which an inventor can appropriately define the concept of the term to describe most appropriately the best method he or she knows for carrying out the disclosure. In addition, unless otherwise defined, technical and scientific terms used herein have the same meaning as commonly understood by those skilled in the art to which the present disclosure pertains. In the following description and the accompanying drawings, descriptions of known functions and components that make the gist of the present disclosure unclear will be omitted. The drawings exemplified below are provided as examples so that the idea of the present disclosure can be sufficiently transferred to those skilled in the art to which the present disclosure pertains. Therefore, the present disclosure is not limited to the accompanying drawings and may be embodied in other forms. In addition, the same reference numerals refer to the same elements throughout the specification. It is noted that the same elements in the drawings are denoted by the same reference numerals throughout the drawings, if possible.

Figure 2:
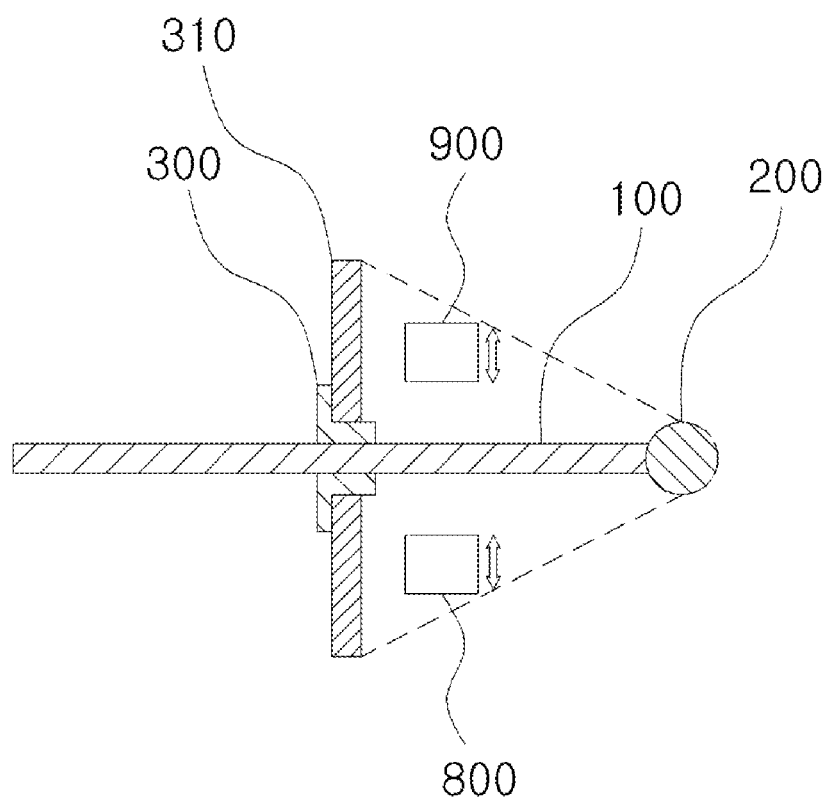
FIG. 2 is a conceptual diagram illustrating a tube weld X-ray inspection device according to another embodiment of the present disclosure.
Figure 3:
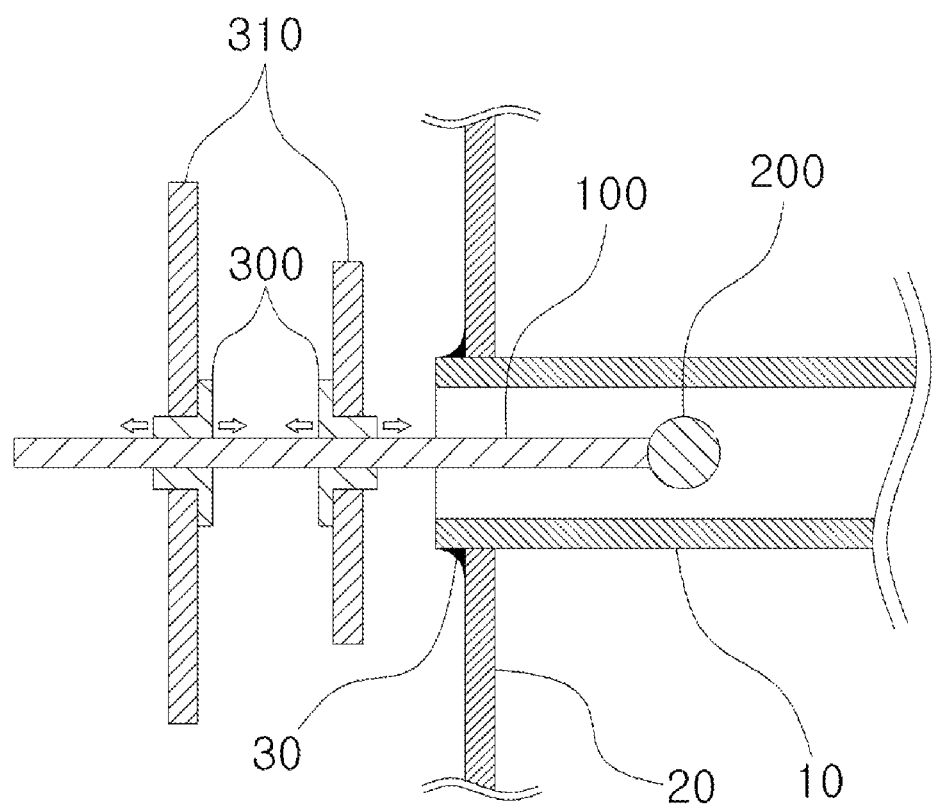
FIG. 3 is a conceptual diagram illustrating a tube weld X-ray inspection device according to still another embodiment of the present disclosure.
Figure 4:
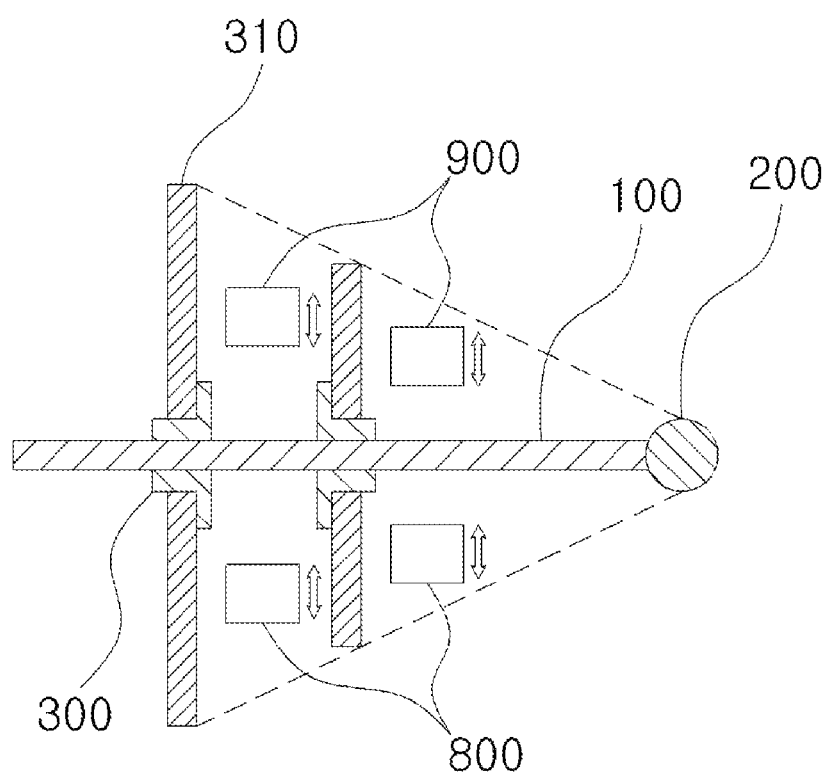
FIG. 4 is a conceptual diagram illustrating a tube weld X-ray inspection device according to yet still another embodiment of the present disclosure.

FIG. 1 is a conceptual diagram illustrating a tube weld X-ray inspection device according to an embodiment of the present disclosure. FIG. 2 is a conceptual diagram illustrating a tube weld X-ray inspection device according to another embodiment of the present disclosure. FIG. 3 is a conceptual diagram illustrating a tube weld X-ray inspection device according to still another embodiment of the present disclosure. FIG. 4 is a conceptual diagram illustrating a tube weld X-ray inspection device according to yet still another embodiment of the present disclosure.

FIG. 1 is a conceptual diagram illustrating a tube weld X-ray inspection device according to an embodiment of the present disclosure. FIG. 1 shows that an X-ray source is inserted into a tube so that the tube weld X-ray inspection device according to the embodiment of the present disclosure inspects a welding part located at an inlet side of the tube.

As shown in FIG. 1, the tube weld X-ray inspection device according to the embodiment of the present disclosure includes an X-ray support 100, an X-ray source 200, and an IP (Image Plate) fixing part 300.

The X-ray support 100 is formed in a length direction so that the X-ray support 100 is inserted into the tube 10.

The X-ray support 100 is for inserting the X-ray source 200 into the tube 10, and any shape capable of being inserted into the tube 10 may be applied, for example, the X-ray support 100 is formed in a rod shape.

The X-ray source 200 is provided at a side of the X-ray support 100 in the length direction thereof, and emits X-rays.

The X-ray source 200 is for being inserted into the tube 10 and emitting X-rays to the inlet side of the tube 10 (the direction from which the X-ray source 200 enters), that is, a welding part 30 between the tube 10 and a tube sheet 20. As long as X-rays can be emitted to the welding part 30 located at the inlet side of the tube 10, various applications, such as omnidirectional radiation and directional radiation, are possible.

The IP fixing part 300 is for fixing an image plate 310 in a direction perpendicular to the axis of the length direction of the X-ray support 100 while being spaced a predetermined distance apart from the X-ray source 200. The image plate 310 absorbs X-rays and stores the X-rays in the form of energy.

The image plate 310 is a plate coated with a photostimulable fluorescent material. The image plate 310 absorbs the X-rays with which the image plate 310 is irradiated and stores the X-rays in the form of energy, and then when the image plate 310 is irradiated with irradiation light such as red light, signal light, such as blue light, in a particular color diverges.

That is, the image plate 310 stores information obtained by an X-ray photographing device, in the form of energy in the image plate 310.

Herein, when the image plate 310 is irradiated with the irradiation light in a particular color, such as red light, the signal light, such as blue light, diffuses and diverges from the irradiated point in all directions. Herein, the diverging particular color may transfer image information, so is called signal light.

The IP fixing part 300 may be realized in various ways as long as the IP fixing part 300 can fix the image plate 310 to a predetermined location.

For example, if the image plate 310 itself can be fixed at a user-desiring location on the axis of the length direction of the X-ray support 100, the image plate 310 itself may be the IP fixing part 300.

The IP fixing part 300 may be realized in various ways, for example, the image plate 310 of a cartridge type is made to be replaceable in a fixed state, and only the image plate 310 is made to be replaceable.

The reason why the IP fixing part 300 is replaceable is that the image plate 310 is a consumable material, and in order to enable various applications, such as the size of the image plate 310 being changed according to the size of the tube.

As shown in FIG. 1, the IP fixing part 300 of the tube weld X-ray inspection device according to the embodiment of the present disclosure is movable in the length direction of the X-ray support 100 along the X-ray support 100.

This is to adjust the location of the IP fixing part 300 when necessary, for example, adjusting the location of the IP fixing part 300 depending on the depth of insertion of the X-ray source 200 into the tube 10, so that more various measurement targets are measured.

As shown in FIG. 1, the IP fixing part 300 of the tube weld X-ray inspection device according to the embodiment of the present disclosure enables the image plate 310 to be attached and detached.

The IP fixing part 300 may be formed in a shape supporting the image plate 310 from the rear (see FIG. 1).

Alternatively, the IP fixing part 300 may be formed in a shape (a casing shape) surrounding the image plate 310 (not shown). Herein, it is preferable that the portion surrounding the front of the image plate 310 (the X-ray source 200 side) is made of a material, for example, a transparent material, which does not seriously interrupt the progress of X-rays.

As shown in FIG. 1, the image plate 310 of the tube weld X-ray inspection device according to the embodiment of the present disclosure is formed in a shape of a plate with a hollow center.

The image plate 310 may have a hollow so that the axis portion of the length direction of the X-ray support 100 is inserted through the hollow portion of the image plate 310 and the image plate 310 is fixed.

This is to facilitate the movement along the X-ray support 100 because the image plate 310 is a consumable material, and also to store the X-rays that have passed through the welding part 30 of the tube 10, in the form of energy in the image plate 310 formed in a single integrated piece.

When the image plate 310 is not formed as a single integrated piece and several attached plates are used as the image plate 310, it is undesirable because image loss or image distortion may occur at the seam portion.

Therefore, it is preferable that the image plate 310 is formed in a shape corresponding to the outer diameter of the tube and that the hollow in the image plate 310 is formed in a shape corresponding to the outer diameter of the X-ray support 100.

For example, when the outer diameter of the tube is circular and the outer diameter of the X-ray support 100 is circular, the image plate 310 is formed in a donut shape.

FIG. 2 is a conceptual diagram illustrating a tube weld X-ray inspection device according to another embodiment of the present disclosure. FIG. 2 shows the embodiment in which a reader, an initialization module, or both a reader and an initialization module are added to the form in FIG. 1.

As shown in FIG. 2, the tube weld X-ray inspection device according to the embodiment of the present disclosure may include a reader 800 that irradiates the image plate 310 with irradiation light, and receives signal light diverging from the image plate 310 to convert the signal light into information in the form of an image.

The reader 800 irradiates the image plate 310 with irradiation light required to obtain image information stored in the image plate 310, a light receiving element receives the signal light diverging from the image plate 310, and the light receiving element converts the received signal light into an electrical signal to generate image information.

When the irradiation light and the signal light have different wavelength ranges, a filter that passes only the signal light is provided between the image plate 310 and the light receiving element.

For example, as the irradiation light, infrared light or light in a red light wavelength range may be used, and as the signal light, ultraviolet light or light in a blue light wavelength range may be used.

The signal light diverging from the image plate 310 laminated with a barium-based mixture and resin is blue light, so when a blue color filter is used, the signal light passes through the filter, and the irradiation light and the ambient light coming from outside are blocked by the filter, thereby reducing image distortion caused by the irradiation light or the ambient light other than the signal light in obtaining an image.

The filter is for obtaining light, mainly, excitation light. When the signal light is blue light and a blue color filter is used, excitation light in a wavelength range from ultraviolet light to blue light (about 500 nm) or lower is absorbed and irradiation light in a higher range is blocked.

The light receiving element is at least one selected from the group of a photodiode (PD) or avalanche photodiode (APD), a multi-pixel photon counter (MPPC), and a photo-multiplier tube (PMD) that convert signal light into electrical signals. Any other light receiving elements having a function of converting light into an electrical signal may be used.

The multi-pixel photon counter (MPPC) is also called a silicon photomultiplier (SiPM), and Geiger-mode avalanche photodiodes are provided in an array.

A process for obtaining an X-ray image by the tube weld X-ray inspection device according to the embodiment of the present disclosure is as follows.

An image plate is mounted and X-rays are emitted>>the emitted X-rays are stored as energy in the image plate>>the image plate is irradiated with irradiation light (e.g., laser beams) by the reader>>the energy stored in the image plate is emitted as signal light>>the obtained signal light signal is converted into a digital signal by the reader>>through image processing, one digital X-ray image is completed After the X-ray image is completed in that order, the X-ray energy remaining in the image plate is removed by irradiating the image plate with light, so that the image plate is used repeatedly.

That is, compared to an analog film that cannot be reused, waste is reduced in terms of environment and cost.

The above-described method is called computed radiography (CR).

According to the CR, an image plate is reusable, and since information is obtained using X-rays with which the image plate is directly irradiated, if an appropriate imaging process is performed, a clearer image can be obtained than when a film is used. In addition, a darkroom required for an existing film-screen detector is not required, so that an inspector is able to conduct inspection more conveniently.

In the tube weld X-ray inspection device according to the embodiment of the present disclosure, as the image plate 310 is rotated and the reader 800 is fixed, or as the reader 800 is rotated and the image plate 310 is fixed, the reader 800 obtains information in the form of an image.

In the case in which the image plate 310 is rotated and the reader 800 is fixed, when the reader 800 is fixed at the X-ray support 100, the X-ray support 100 is fixed and thus the reader 800 is fixed, and the image plate 310 is rotated on the X-ray support 100.

In the case in which the reader 800 is rotated and the image plate 310 is fixed, when the image plate 310 is fixed at the X-ray support 100, the X-ray support 100 is fixed and thus the image plate 310 is fixed, and the reader 800 is rotated around the X-ray support 100.

The case in which the X-ray support 100 is fixed has been described above as an example, but the present disclosure is not limited thereto and various applications, such as the X-ray support 100 being rotatable, are possible.

As shown in FIG. 2, the reader 800 of the tube weld X-ray inspection device according to the embodiment of the present disclosure moves to the outside of the region for the image plate 310 before X-ray photography, and moves to the position at which image information of the image plate 310 is extractable, after X-ray photography.

The region for the image plate 310 refers to a region in which the X-rays emitted from the X-ray source 200 reach the image plate 310. In FIG. 2, the region for the image plate 310 is an inside region of the dotted line.

That is, the outside of the region for the image plate 310 refers to a region (the outside of the dotted line) (which does not intercept the X-rays) in which the X-rays emitted from the X-ray source 200 are not interrupted until the X-rays reach the image plate 310.

The example in FIG. 2 shows that the reader 800 is movable only in an upward-downward direction, but the present disclosure is not limited thereto. Various applications are possible as long as the reader 800 can move so as not to interrupt photographing during X-ray photography, for example, move in an upward-downward direction and then in a forward-backward direction, and can move to the position at which image information of the image plate 310 is extractable so as to obtain an image after X-ray photography.

The example in FIG. 2 shows that ahead of the image plate 310, the reader 800 moves to the position at which image information of the image plate 310 is extractable, but the present disclosure is not limited thereto. Various applications are possible as long as the image information can be extracted from the image plate 310, for example, behind the image plate 310, the reader 800 moves to the position at which the image information of the image plate 310 is extractable.

As shown in FIG. 2, the tube weld X-ray inspection device according to the embodiment of the present disclosure may include an initialization module 900 that irradiates the image plate 310 with light to make the image plate 310 be in a re-photographable state.

The initialization module 900 is for initializing the energy stored in the image plate 310, and removes the energy remaining in the image plate 310 by irradiating the image plate 310 with light.

In the tube weld X-ray inspection device according to the embodiment of the present disclosure, as the image plate 310 is rotated and the initialization module 900 is fixed, or as the initialization module 900 is rotated and the image plate 310 is fixed, the initialization module 900 makes the image plate 310 be in the re-photographable state.

In the case in which the image plate 310 is rotated and the initialization module 900 is fixed, when the initialization module 900 is fixed at the X-ray support 100, the X-ray support 100 is fixed and thus the initialization module 900 is fixed, and the image plate 310 is rotated on the X-ray support 100.

In the case in which the initialization module 900 is rotated and the image plate 310 is fixed, when the image plate 310 is fixed at the X-ray support 100, the X-ray support 100 is fixed and thus the image plate 310 is fixed, and the initialization module 900 is rotated around the X-ray support 100.

The case in which the X-ray support 100 is fixed has been described above as an example, but the present disclosure is not limited thereto and various applications, such as the X-ray support 100 being rotatable, are possible.

As shown in FIG. 2, the initialization module 900 of the tube weld X-ray inspection device according to the embodiment of the present disclosure moves to the outside of the region for the image plate 310 before X-ray photography, and moves to the position at which the image plate 310 can be made to be in the re-photographable state after X-ray photography.

The region for the image plate 310 refers to a region in which the X-rays emitted from the X-ray source 200 reach the image plate 310. In FIG. 2, the region for the image plate 310 is an inside region of the dotted line.

That is, the outside of the region for the image plate 310 refers to a region (the outside of the dotted line) (which does not intercept the X-rays) in which the X-rays emitted from the X-ray source 200 are not interrupted until the X-rays reach the image plate 310.

The example in FIG. 2 shows that the initialization module 900 is movable only in an upward-downward direction, but the present disclosure is not limited thereto. Various applications are possible as long as the initialization module 900 can move so as not to interrupt photographing during X-ray photography, for example, move in an upward-downward direction and then in a forward-backward direction, and can move to the position at which the image plate 310 can be made to be in the re-photographable state so as to initialize the image plate 310.

The example in FIG. 2 shows that ahead of the image plate 310, the initialization module 900 moves to the position at which the image plate 310 can be made to be in the re-photographable state, but the present disclosure is not limited thereto. Various applications are possible as long as the image plate 310 can be made to be in the re-photographable state, for example, behind the image plate 310, the initialization module 900 moves to the position at which the image plate 310 can be made to be in the re-photographable state.

FIG. 3 is a conceptual diagram illustrating a tube weld X-ray inspection device according to an embodiment of the present disclosure. FIG. 3 shows that an X-ray source is inserted into a tube so that the tube weld X-ray inspection device according to the embodiment of the present disclosure inspects a welding part located at an inlet side of the tube.

As shown in FIG. 3, the tube weld X-ray inspection device according to the embodiment of the present disclosure includes an X-ray support 100, an X-ray source 200, and IP fixing parts 300.

The X-ray support 100 is formed in a length direction so that the X-ray support 100 is inserted into the tube 10.

The X-ray support 100 is for inserting the X-ray source 200 into the tube, and any shape capable of being inserted into the tube may be applied, for example, the X-ray support 100 is formed in a rod shape.

The X-ray source 200 is provided at a side of the X-ray support 100 in the length direction thereof, and emits X-rays.

The X-ray source 200 is for being inserted into the tube and emitting X-rays to the inlet side of the tube (the direction from which the X-ray source 200 enters), that is, a welding part 30 between the tube 10 and a tube sheet 20. As long as X-rays can be emitted to the welding part 30 located at the inlet side of the tube 10, various applications, such as omnidirectional radiation and directional radiation, are possible.

The IP fixing parts 300 are for fixing respective image plates 310 in a direction perpendicular to the axis of the length direction of the X-ray support 100 while being spaced respective predetermined distances apart from the X-ray source 200. The image plates 310 absorb X-rays and store the X-rays in the form of energy. A plurality of the IP fixing parts 300 are provided such that the plurality of the IP fixing parts 300 are spaced apart from each other by a predetermined distance.

Each of the image plates 310 is a plate coated with a photo-stimulable fluorescent material. The image plates 310 absorb the X-rays with which the image plates 310 are irradiated and store the X-rays in the form of energy, and then when the image plates 310 are irradiated with irradiation light such as red light, signal light, such as blue light, in a particular color diverges.

That is, the image plates 310 store information obtained by an X-ray photographing device, in the form of energy in the image plates 310.

Herein, when the image plates 310 are irradiated with the irradiation light in a particular color, such as red light, the signal light, such as blue light, diffuses and diverges from the irradiated points in all directions. Herein, the diverging particular color may transfer image information, so is called signal light.

The IP fixing parts 300 may be realized in various ways as long as the IP fixing parts 300 can fix the image plates 310 to predetermined locations.

For example, if the image plates 310 themselves can be fixed at user-desiring locations on the axis of the length direction of the X-ray support 100, the image plates 310 themselves may be the IP fixing parts 300.

The IP fixing parts 300 may be realized in various ways, for example, the image plates 310 of a cartridge type are made to be replaceable in a fixed state, and only the image plates 310 are made to be replaceable.

The reason why the IP fixing parts 300 are replaceable is that the image plates 310 are a consumable material, and in order to enable various applications, such as the sizes of the image plates 310 being changed according to the size of the tube.

Providing the plurality of the IP fixing parts 300 is for more accurate measurement. Herein, it is preferable that the IP fixing parts 300 are made of a material through which some of the X-rays can pass.

The tube weld X-ray inspection device according to the embodiment of the present disclosure can take n (n is a natural number equal to or greater than 2) images simultaneously by performing one X-ray photography, and combines the n images obtained from the n image plates 310 photographed in that way, so that a three-dimensional image highlighting a problem portion can be obtained.

As shown in FIG. 3, the IP fixing parts 300 of the tube weld X-ray inspection device according to the embodiment of the present disclosure are movable in the length direction of the X-ray support 100 along the X-ray support 100.

This is to adjust the locations of the IP fixing parts 300 when necessary, for example, adjusting the locations of the IP fixing parts 300 depending on the depth of insertion of the X-ray source 200 into the tube 10, so that more various measurement targets are measured.

As shown in FIG. 3, the IP fixing parts 300 of the tube weld X-ray inspection device according to the embodiment of the present disclosure enable the image plates 310 to be attached and detached.

The IP fixing parts 300 may be formed in a shape supporting the respective image plates 310 from the rear (see FIG. 3).

Alternatively, the IP fixing parts 300 may be formed in a shape (a casing shape) surrounding the respective image plates 310 (not shown). Herein, it is preferable that the portion surrounding the front of each of the image plates 310 (the X-ray source 200 side) is made of a material, for example, a transparent material, which does not seriously interrupt the progress of X-rays.

As shown in FIG. 3, each of the image plates 310 of the tube weld X-ray inspection device according to the embodiment of the present disclosure is formed in a shape of a plate with a hollow center.

Each image plate 310 may have a hollow so that the axis portion of the length direction of the X-ray support 100 is inserted through the hollow portion of each image plate 310 and each image plate 310 is fixed.

This is to facilitate the movement along the X-ray support 100 because the image plates 310 are a consumable material, and also to store the X-rays that have passed through the welding part 30 of the tube 10, in the form of energy in the image plates 310 each formed in a single integrated piece.

When each image plate 310 is not formed as a single integrated piece and several attached plates are used as each image plate 310, it is undesirable because image loss or image distortion may occur at the seam portion.

Therefore, it is preferable that each image plate 310 is formed in a shape corresponding to the outer diameter of the tube and that the hollow in each image plate 310 is formed in a shape corresponding to the outer diameter of the X-ray support 100.

For example, when the outer diameter of the tube is circular and the outer diameter of the X-ray support 100 is circular, the image plates 310 are formed in a donut shape.

FIG. 4 is a conceptual diagram illustrating a tube weld X-ray inspection device according to yet still another embodiment of the present disclosure. FIG. 4 shows the embodiment in which readers, initialization modules, or readers and initialization modules are added to the form in FIG. 3.

As shown in FIG. 4, the tube weld X-ray inspection device according to the embodiment of the present disclosure may include readers 800 that irradiate the respective image plates 310 with irradiation light, and receive signal light diverging from the image plates 310 to convert the signal light into information in the form of an image.

The readers 800 irradiate the image plates 310 with irradiation light required to obtain image information stored in the image plates 310, light receiving elements receive the signal light diverging from the image plates 310, and the light receiving elements convert the received signal light into electrical signals to generate image information.

When the irradiation light and the signal light have different wavelength ranges, filters that pass only the signal light are provided between the image plates 310 and the light receiving elements.

For example, as the irradiation light, infrared light or light in a red light wavelength range may be used, and as the signal light, ultraviolet light or light in a blue light wavelength range may be used.

The signal light diverging from the image plates 310 laminated with a barium-based mixture and resin is blue light, so when blue color filters are used, the signal light passes through the filters, and the irradiation light and the ambient light coming from outside are blocked by the filters, thereby reducing image distortion caused by the irradiation light or the ambient light other than the signal light in obtaining an image.

Each of the filters is for obtaining light, mainly, excitation light. When the signal light is blue light and blue color filters are used, excitation light in a wavelength range from ultraviolet if) light to blue light (about 500 nm) or lower is absorbed and irradiation light in a higher range is blocked.

The light receiving elements are at least one selected from the group of a photodiode (PD) or avalanche photodiode (APD), a multi-pixel photon counter (MPPC), and a photomultiplier tube (PMD) that convert signal light into electrical signals. Any other light receiving elements having a function of converting light into an electrical signal may be used.

The multi-pixel photon counter (MPPC) is also called a silicon photomultiplier (SiPM), and Geiger-mode avalanche photodiodes are provided in an array.

A process for obtaining an X-ray image by the tube weld X-ray inspection device according to the embodiment of the present disclosure is as follows.

Image plates are mounted and X-rays are emitted>>the emitted X-rays are stored as energy in the image plates>>the image plates are irradiated with irradiation light (e.g., laser beams) by the readers>>the energy stored in the image plates is emitted as signal light>>the obtained signal light signals are converted into digital signals by the readers>>through image processing, one digital X-ray image is completed After the X-ray image is completed in that order, the X-ray energy remaining in the image plates is removed by irradiating the image plates with light, so that the image plates are used repeatedly.

That is, compared to an analog film that cannot be reused, waste is reduced in terms of environment and cost.

The above-described method is called computed radiography (CR).

According to the CR, an image plate is reusable, and since information is obtained using X-rays with which the image plate is directly irradiated, if an appropriate imaging process is performed, a clearer image can be obtained than when a film is used. In addition, a darkroom required for an existing film-screen detector is not required, so that an inspector is able to conduct inspection more conveniently.

In the tube weld X-ray inspection device according to the embodiment of the present disclosure, as the image plates 310 are rotated and the readers 800 are fixed, or as the readers 800 are rotated and the image plates 310 are fixed, the readers 800 obtain information in the form of an image.

In the case in which the image plates 310 are rotated and the readers 800 are fixed, when the readers 800 are fixed at the X-ray support 100, the X-ray support 100 is fixed and thus the readers 800 are fixed, and the image plates 310 are rotated on the X-ray support 100.

In the case in which the readers 800 are rotated and the image plates 310 are fixed, when the image plates 310 are fixed at the X-ray support 100, the X-ray support 100 is fixed and thus the image plates 310 are fixed, and the readers 800 are rotated around the X-ray support 100.

The case in which the X-ray support 100 is fixed has been described above as an example, but the present disclosure is not limited thereto and various applications, such as the X-ray support 100 being rotatable, are possible.

As shown in FIG. 4, the readers 800 of the tube weld X-ray inspection device according to the embodiment of the present disclosure move to the outside of the region for the image plates 310 before X-ray photography, and move to the positions at which image information of the image plates 310 is extractable, after X-ray photography.

The region for the image plates 310 refers to a region in which the X-rays emitted from the X-ray source 200 reach the image plates 310. In FIG. 4, the region for the image plates 310 is an inside region of the dotted line.

That is, the outside of the region for the image plates 310 refers to a region (the outside of the dotted line) (which does not intercept the X-rays) in which the X-rays emitted from the X-ray source 200 are not interrupted until the X-rays reach the image plates 310.

The example in FIG. 4 shows that each reader 800 is movable only in an upward-downward direction, but the present disclosure is not limited thereto. Various applications are possible as long as each reader 800 can move so as not to interrupt photographing during X-ray photography, for example, move in an upward-downward direction and then in a forward-backward direction, and can move to the position at which image information of the matched image plate 310 is extractable so as to obtain an image after X-ray photography.

The example in FIG. 4 shows that ahead of the matched image plate 310, each reader 800 moves to the position at which image information of the matched image plate 310 is extractable, but the present disclosure is not limited thereto. Various applications are possible as long as the image information can be extracted from the matched image plate 310, for example, behind the matched image plate 310, each reader 800 moves to the position at which the image information of the matched image plate 310 is extractable.

As shown in FIG. 4, the tube weld X-ray inspection device according to the embodiment of the present disclosure may include initialization modules 900 that irradiate the respective image plates 310 with light to make the image plates 310 be in a re-photographable state.

The initialization modules 900 are for initializing the energy stored in the image plates 310, and remove the energy remaining in the image plates 310 by irradiating the image plates 310 with light.

In the tube weld X-ray inspection device according to the embodiment of the present disclosure, as the image plates 310 are rotated and the initialization modules 900 are fixed, or as the initialization modules 900 are rotated and the image plates 310 are fixed, the initialization modules 900 make the image plate 310 be in the re-photographable state.

In the case in which the image plates 310 are rotated and the initialization modules 900 are fixed, when the initialization modules 900 are fixed at the X-ray support 100, the X-ray support 100 is fixed and thus the initialization modules 900 are fixed, and the image plates 310 are rotated on the X-ray support 100.

In the case in which the initialization modules 900 are rotated and the image plates 310 are fixed, when the image plates 310 are fixed at the X-ray support 100, the X-ray support 100 is fixed and thus the image plates 310 are fixed, and the initialization modules 900 are rotated around the X-ray support 100.

The case in which the X-ray support 100 is fixed has been described above as an example, but the present disclosure is not limited thereto and various applications, such as the X-ray support 100 being rotatable, are possible.

As shown in FIG. 4, the initialization modules 900 of the tube weld X-ray inspection device according to the embodiment of the present disclosure move to the outside of the region for the image plates 310 before X-ray photography, and move to the positions at which the image plates 310 can be made to be in the re-photographable state after X-ray photography.

The region for the image plates 310 refers to a region in which the X-rays emitted from the X-ray source 200 reach the image plates 310. In FIG. 4, the region for the image plates 310 is an inside region of the dotted line.

That is, the outside of the region for the image plates 310 refers to a region (the outside of the dotted line) (which does not intercept the X-rays) in which the X-rays emitted from the X-ray source 200 are not interrupted until the X-rays reach the image plates 310.

The example in FIG. 4 shows that each initialization module 900 is movable only in an upward-downward direction, but the present disclosure is not limited thereto. Various applications are possible as long as each initialization module 900 can move so as not to interrupt photographing during X-ray photography, for example, move in an upward-downward direction and then in a forward-backward direction, and can move to the position at which the matched image plate 310 can be made to be in the re-photographable state so as to initialize the matched image plate 310.

The example in FIG. 4 shows that ahead of the matched image plate 310, each initialization module 900 moves to the position at which the image plate 310 can be made to be in the re-photographable state, but the present disclosure is not limited thereto. Various applications are possible as long as the matched image plate 310 can be made to be in the re-photographable state, for example, behind the matched image plate 310, each initialization module 900 moves to the position at which the matched image plate 310 can be made to be in the re-photographable state.

The present disclosure is not limited to the above-described embodiments and has a wide range of application. Various modifications are possible without departing from the substance of the present disclosure set forth in the accompanying claims.

What is claimed is:

1. A tube weld X-ray inspection device for inspecting a tube, the tube weld X-ray inspection device comprising:
   an X-ray support configured to be inserted into a tube being inspected;
   an X-ray source provided at a side of the X-ray support in a length direction of the X-ray support, the X-ray source being configured to emit X-rays;
   an image plate configured to absorb the X-rays and to store the X-rays in a form of energy; and
   an image plate fixing part configured to fix the image plate in a direction perpendicular to an axis of the length direction of the X-ray support while being spaced a predetermined distance from the X-ray source.

2. The tube weld X-ray inspection device of claim 1, wherein the image plate fixing part is movable in the length direction of the X-ray support along the X-ray support.

3. The tube weld X-ray inspection device of claim 1, wherein the image plate fixing part enables the image plate to be attached and detached.

4. The tube weld X-ray inspection device of claim 1, wherein the image plate has a hollow center.

5. The tube weld X-ray inspection device of claim 1, further comprising a reader configured to irradiate the image plate with an irradiation light and to receive a signal light diverging from the image plate to convert the signal light into information in a form of an image.

6. The tube weld X-ray inspection device of claim 5, wherein, as the image plate is rotated and the reader is fixed, or as the reader is rotated and the image plate is fixed, the reader obtains the information in the form of the image.

7. The tube weld X-ray inspection device of claim 5, wherein the reader moves to an outside of a region for the image plate before X-ray photography, and moves to a position at which image information of the image plate is extractable, after the X-ray photography.

8. The tube weld X-ray inspection device of claim 5, further comprising an initializer configured to irradiate the image plate with light to make the image plate be in a re-photographable state.

9. The tube weld X-ray inspection device of claim 8, wherein, as the image plate is rotated and the initializer is fixed, or as the initializer is rotated and the image plate is fixed, the initializer makes the image plate be in the re-photographable state.

10. The tube weld X-ray inspection device of claim 8, wherein the initializer moves to an outside of a region for the image plate before X-ray photography, and moves to a position at which the image plate is made to be in the re-photographable state, after the X-ray photography.

11. A tube weld X-ray inspection device for inspecting a tube, the tube weld X-ray inspection device comprising:
   an X-ray support configured to be inserted into a tube being inspected;
   an X-ray source provided at a side of the X-ray support in a length direction of the X-ray support, the X-ray source being configured to emit X-rays;
   an image plate configured to absorb the X-rays and to store the X-rays in a form of energy; and
   a plurality of image plate fixing parts, each of the plurality of image plate fixing parts configured to fix the image plate in a direction perpendicular to an axis of the length direction of the X-ray support while being spaced a predetermined distance from the X-ray source,
   wherein the plurality of image plate fixing parts are provided such that the plurality of image plate fixing parts are spaced apart from each other by a predetermined distance.

12. The tube weld X-ray inspection device of claim 11, wherein each of the plurality of image plate fixing parts is movable in the length direction of the X-ray support along the X-ray support.

13. The tube weld X-ray inspection device of claim 11, wherein each of the plurality of image plate fixing parts enables the image plate to be attached and detached.

14. The tube weld X-ray inspection device of claim 11, wherein the image plate has a hollow center.

15. The tube weld X-ray inspection device of claim 11, further comprising a reader configured to irradiate the image plate with an irradiation light and to receive a signal light diverging from the image plate to convert the signal light into information in a form of an image.

16. The tube weld X-ray inspection device of claim 15, wherein, as the image plate is rotated and the reader is fixed, or as the reader is rotated and the image plate is fixed, the reader obtains the information in the form of the image.

17. The tube weld X-ray inspection device of claim 15, wherein the reader moves to an outside of a region for the image plate before X-ray photography, and moves to a position at which image information of the image plate is extractable, after the X-ray photography.

18. The tube weld X-ray inspection device of claim 15, further comprising an initializer configured to irradiate the image plate with light to make the image plate be in a re-photographable state.

19. The tube weld X-ray inspection device of claim 18, wherein, as the image plate is rotated and the initializer is fixed, or as the initializer is rotated and the image plate is fixed, the initializer makes the image plate be in the re-photographable state.

20. The tube weld X-ray inspection device of claim 18, wherein the initializer moves to an outside of a region for the image plate before X-ray photography, and moves to a position at which the image plate is made to be in the re-photographable state, after the X-ray photography.

* * * * *